(12) United States Patent
Goble

(10) Patent No.: US 6,547,786 B1
(45) Date of Patent: Apr. 15, 2003

(54) ELECTROSURGERY SYSTEM AND INSTRUMENT

(75) Inventor: Colin Charles Owen Goble, Penarth (GB)

(73) Assignee: Gyrus Medical, St. Mellons (GB)

( * ) Notice: Subject to any disclaimer, the term of this patent is extended or adjusted under 35 U.S.C. 154(b) by 0 days.

(21) Appl. No.: 09/572,338

(22) Filed: May 18, 2000

Related U.S. Application Data (63) Continuation-in-part of application No. 09/343,544, filed on Jun. 30, 1999.

(30) Foreign Application Priority Data

May 21, 1999 (GB) ............................................. 9911954

(51) Int. Cl.⁷ ............................................. A61B 18/04
(52) U.S. Cl. ............................................. 606/34; 606/32
(58) Field of Search ............................. 606/28–31, 34, 606/41, 42; 607/101, 102; 600/549

(56) References Cited

U.S. PATENT DOCUMENTS

| | | | |
|---|---|---|---|
| 4,188,927 A | 2/1980 | Harris | |
| 4,271,837 A | 6/1981 | Schuler | |
| 4,411,266 A | * 10/1983 | Cosman | 606/49 |
| 4,860,745 A | 8/1989 | Farin et al. | |
| 4,907,589 A | * 3/1990 | Cosman | 606/34 |
| 5,133,711 A | 7/1992 | Hagen | |

FOREIGN PATENT DOCUMENTS

| | | |
|---|---|---|
| DE | 198 27 318 A 1 | 12/1999 |
| EP | 0 754 437 A2 | 1/1996 |
| EP | 0 754 437 A2 | 1/1997 |
| GB | 897961 | 6/1962 |
| WO | WO 95/09576 | 4/1994 |
| WO | WO 95/09576 | 4/1995 |
| WO | WO 96/39967 | 12/1996 |

* cited by examiner

*Primary Examiner*—Michael Peffley (57) ABSTRACT

In an electrosurgery system having a radio frequency generator and an instrument with a treatment electrode, the generator includes a circuit for sensing thermionic emission from the electrode as means of controlling the supply of radio frequency power to the electrode. Thermionic emission is sensed by detecting d.c. voltage at the output of the generator, or an a.c. representation of the d.c. voltage, using a detector with an isolated output, and generator output power is controlled so as to limit the d.c. voltage or the a.c. representation to a predetermined threshold. Accordingly, the temperature of the electrode can be limited to avoid electrode destruction. The invention also has application to reducing nerve stimulation due to electrosurgical treatment.

4 Claims, 4 Drawing Sheets

ELECTROSURGERY SYSTEM AND INSTRUMENT

This is a Continuation-in-Part of application Ser. No. 09/343,544 filed Jun. 30, 1999. The entire disclosure of the prior application is hereby incorporated by reference herein in its entirety.

FIELD OF THE INVENTION

This invention relates to an electrosurgery system, an electrosurgical instrument, and a method of performing electrosurgery.

BACKGROUND OF THE INVENTION

The cutting or removal of tissue electrosurgically using an instrument having a tip with one or more active electrodes supplied with a radio frequency voltage usually involves cell rupture as a result of arcs between the active electrode and the tissue being treated or, in the case of underwater electrosurgery, between the active electrode or electrodes and a conductive liquid overlying the tissue to be treated. As described in European Patent Application No. 0754437A, electrode destruction can occur if sufficient radio frequency power is supplied to an electrode to cause burning or melting of the electrode material, and this can be avoided by sensing peak electrode voltage and applying feedback to reduce the applied power so as to set a maximum peak voltage. It will be understood that for a given power setting, the temperature of the electrode depends on the rate at which heat can be dissipated which, in turn, depends on such variables as the degree of tissue engagement, electrode structure, and fluid flow around the electrode. Consequently, to avoid electrode destruction the peak voltage limit must be set at a sufficiently low level to prevent damage in the worst case dissipation situations, i.e. when there is an absence of cooling fluid and/or the electrode is surrounded by tissue.

It is known that the arcing at the electrode can cause nerve stimulation. This is due to the thermionic effect when the electrode is heated. Since the use of a coupling capacitor between the radio frequency source in the generator and the electrode is mandatory, the electrode is isolated, allowing charge to build up on the capacitor, which produces nerve stimulation when the electrode touches tissue or conductive fluid overlying the tissue.

SUMMARY OF THE INVENTION

The invention is based on the recognition that the thermionic effect is temperature dependent and, therefore, may be used as a indication of electrode temperature.

Accordingly, the invention provides an electrosurgery system comprising a generator which includes a source of radio frequency energy for feeding to a treatment electrode of an electrosurgical instrument, wherein the generator includes a circuit for sensing thermionic emission from the electrode.

The invention also includes an electrosurgery system comprising a generator including a source of radio frequency (r.f.) energy and, coupled to the generator, an electrosurgical instrument having a treatment electrode, wherein the system includes a d.c. voltage detector arranged to detect a d.c. offset in excess of 2 volts on the treatment electrode, and, coupled to the detector, a control circuit for controlling the r.f. energy applied to the instrument in response to the d.c. offset. In this way, the level of the d.c. voltage at the treatment electrode due the thermionic effect may be limited as a means, for instance, of controlling electrode temperature. Indeed the association of the thermionic effect with arcing and, in particular, arcing at such a level and in such surroundings that the treatment electrode becomes very hot, can be used in accordance with the invention for electrode overheat protection. This, in turn, allows an electrode used in surroundings having other than worst case heat dissipation to be operated at a higher temperature than would be possible using the prior art voltage-sensing technique, with a consequent increase in the rate at which tissue may be cut or removed.

Typically, for overheat protection, the control circuit and detector are operable to limit the d.c. offset to a predetermined d.c. voltage level in the region of from 50 V to 100 V. In practice, the actual voltage level depends on electrode configuration and electrode material. Thus, if a platinum electrode is used, the voltage limit is set to that which occurs when the electrode voltage approaches 1600° C., the melting point of platinum.

Alternatively, the maximum d.c. offset voltage may be set to a much lower value to reduce nerve stimulation in sensitive sites such as in neurosurgery, surgery in the region of the spine, and in muscle tissue.

In a preferred embodiment of the invention, the generator has an output terminal connectible to the treatment electrode and the detector has (i) a detection input which is connected to the output terminal and (ii) an isolation device connecting the detector to the control circuit. The detector may be powered from the generator r.f. output energy by having a power supply circuit coupled to the generator output terminal and including a rectifier for rectifying the r.f. electrosurgery signal applied to the output terminal. This is permissible since the thermionic effect does not occur until the r.f. output voltage reaches a level consistent with arcing. The fact that the detector does not function at lower voltages is, as a result, no disadvantage. Typically, to achieve isolation at the output of the detector, it comprises an oscillator for generating an alternating measurement signal representative of the d.c. offset, and the isolation device comprises an opto-isolator coupled to receive the alternating measurement signal and to feed it to the control circuit. The preferred detector also includes a reverse polarity d.c. offset detector as a fault condition indicator which can be used to disable the r.f. source when, for instance, in use of a bipolar electrode assembly in a conductive fluid field, a lack of fluid causes d.c. polarity reversal.

According to a second aspect of the invention, an electrosurgical generator including a source of r.f. energy, an active output terminal, a return output terminal and a d.c. isolation capacitor between the source and the active output terminal, has a d.c. offset detector having a shunt input connected on the output terminal side of the isolation capacitor for detecting d.c. voltages in excess of 2 volts, and a control circuit coupled to the source for controlling the r.f. energy applied to the active output terminal in response to the d.c. offset voltage at the shunt input.

According to a third aspect of the invention, a method of performing electrosurgical tissue cutting or ablation comprises applying r.f. energy to an electrosurgical instrument so as to promote arcing at a treatment electrode of the instrument, and regulating the level of applied energy according to the d.c. voltage attained at the electrode due to thermionic emission from the electrode. The r.f. energy may be regulated to maximise the temperature of the electrode without substantial electrode damage, typically by limiting the d.c. voltage to a threshold value of less than 100 V.

In the above-described preferred embodiment, detection of the thermionic effect occurs as a result of the continual discharge of capacitors in the output stage of the generator through a high value resistance, the detected DC voltage across the electrodes being representative of this effect. Since this detection technique is limited by the time constant for the discharge of the capacitors in the output stage, it has the disadvantage of having a relatively slow response time. The time constant is the product of the capacitance and resistance in the circuit. The capacitors are necessarily large to reduce output impedance, and the shunt resistance connected across the output terminals is large to prevent the flow of significant direct current through the patient.

A further embodiment provides an alternative technique for detecting thermionic emission from the active electrode in which an alternating current phenomenon affected by thermionic emissions is detected, obviating the need for a DC conducting path across the output terminals of the generator. Accordingly, a further aspect of the present invention provides a modulated generator output, and a detection circuit coupled to the generator output by means of a coupling which does not include any DC conductive path, the detection circuit being tuned to the frequency of the modulation of the generator output, wherein thermionic emissions from the active electrode cause manifestation of the modulation in the generator output in the detection circuit.

In a preferred embodiment the amplitude of the generator output is modulated in a manner such that, in the absence of any thermionic effect, the average value of the generator output as measured over a single cycle of the generator output remains constant; the existence of thermionic emissions causes the average value of the generator output measured over a single cycle to vary at the frequency of the generator amplitude modulation, and the amplitude of this variation in average value corresponds to the extent of the thermionic effect. The detection circuit may be provided by a suitably tuned resonant circuit and a detector which is inductively coupled to the generator output stage to detect a voltage in the resonant circuit which results from thermionic emission.

The invention will now be described below by way of example with reference to the drawings.

DETAILED DESCRIPTION OF THE PREFERRED EMBODIMENTS

Figure 1:
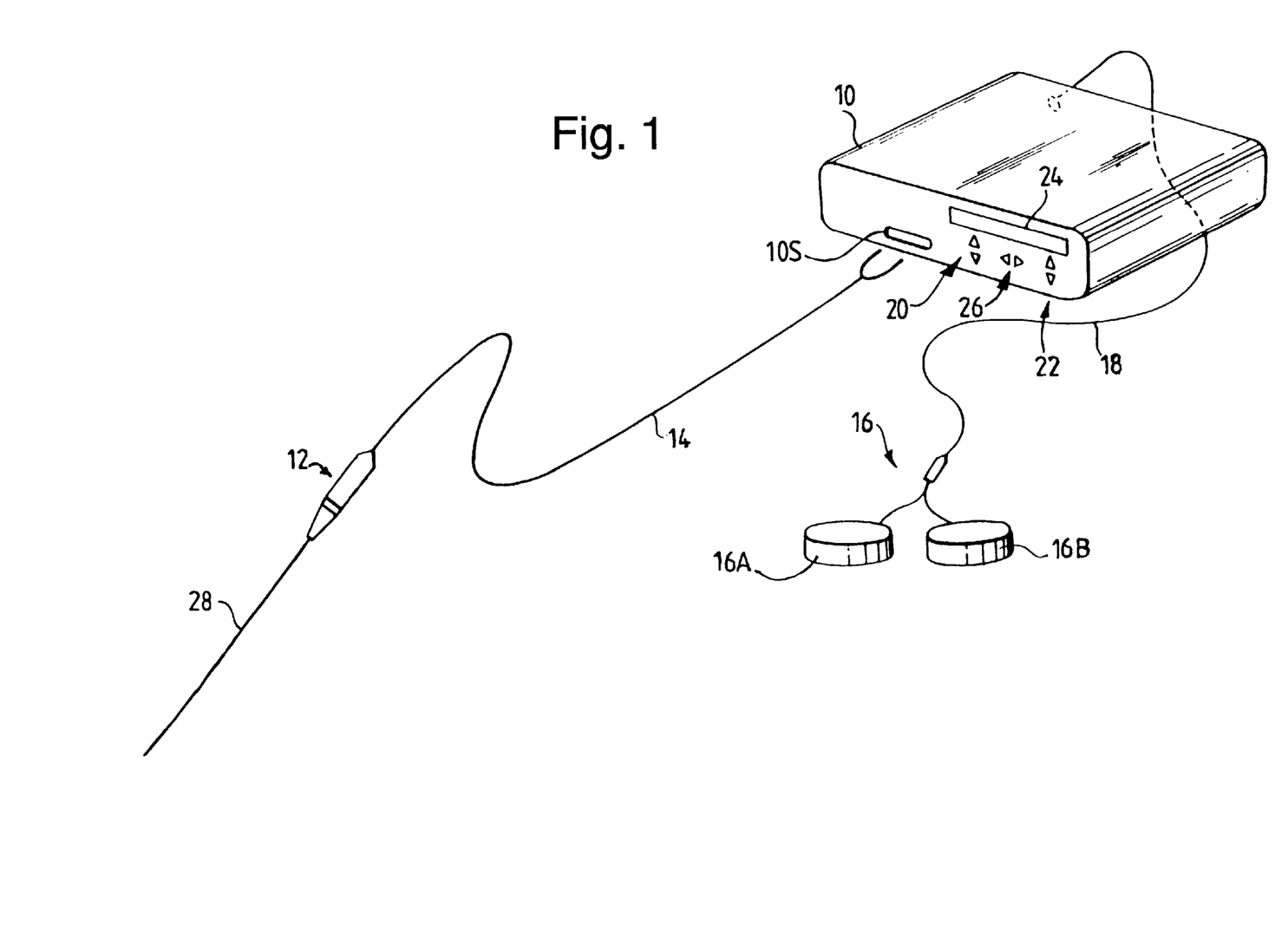
FIG. 1 is a diagram showing an electrosurgery system in accordance with the invention.

The present invention is applicable to both wet and dry field electrosurgery. Referring to FIG. 1, the system comprises a generator 10 having an output socket 10S which provides a radio frequency (r.f.) output for an electrosurgical instrument in the form of a handpiece 12 via a connection cord 14. Activation of the generator may be performed from the handpiece 12 via a control connection in cord 14 or by means of a foot switch unit 16, as shown, connected separately to the rear of the generator 10 by a foot switch connection cord 18. In the illustrated embodiment, foot switch unit 16 has two foot switches 16A and 16B for selecting a desiccation mode and a vaporisation mode of the generator respectively. The generator front panel has push buttons 20 and 22 for respectively setting desiccation and vaporisation power levels, which are indicated in a display 24. Push buttons 26 are provided as alternative means for mode selection.

Figure 2:
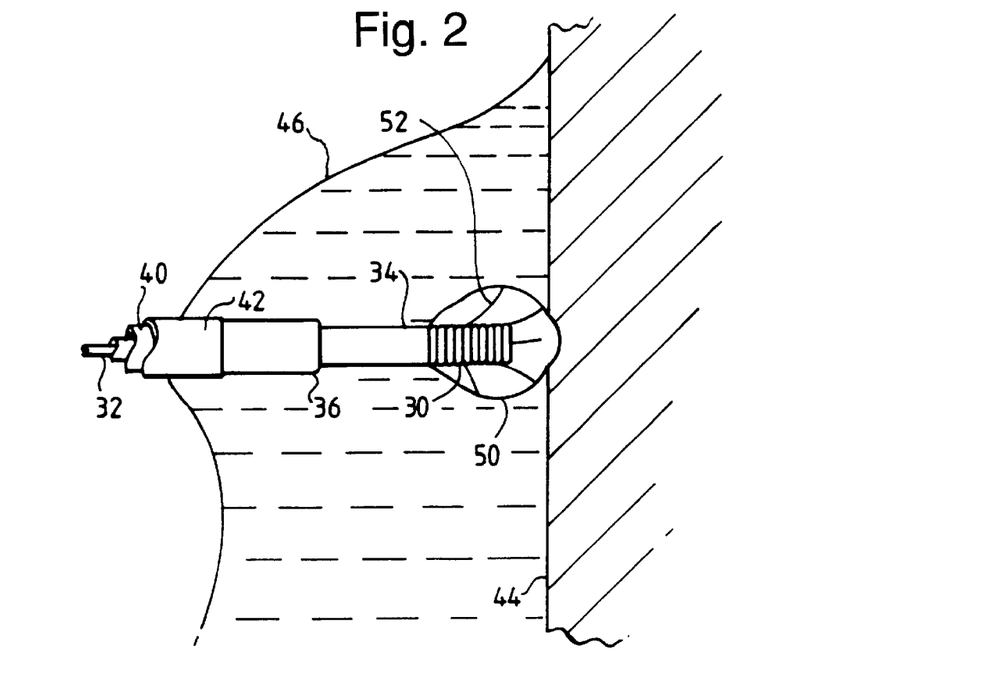
FIG. 2 is a fragmentary view of an electrode assembly for tissue ablation, shown in use immersed in a conductive liquid.

Handpiece 12 mounts a detachable electrode assembly 28 having a dual electrode structure, as shown in the fragmentary view of FIG. 2.

FIG. 2 is an enlarged view of the distal end of the electrode assembly 28. At its extreme distal end the assembly has an active electrode 30 which, in this embodiment, is formed as a coiled wire connected to a central conductor 32. The coil wire may be made of platinum. Proximally of the active electrode 30 and spaced from the latter by a longitudinally and radially extending ceramic insulator 34 is a return electrode 36. The return electrode 36 is arranged coaxially around the inner conductor 32 as a sleeve which extends as a tubular shaft 40 to the proximal end of the assembly 28 (see FIG. 1) where it is connected in the handpiece 12 to a conductor in the connection cord 14. Similarly, the inner conductor 32 extends to the handpiece 12 and is connected to another conductor in cord 14. Insulation between the inner conductor 32 and the return electrode 36 is provided by the insulator 34 which is constructed as a sleeve extending inside the return electrode to insulate an inner extension (not shown) of the active electrode 30 from the return electrode 36. To promote greater power density at the active electrode than at the return electrode, the surface area of the return electrode is considerably greater than that of the active electrode. With regard to typical dimensions, at the distal end of the electrode assembly, the diameter of the return electrode is typically in the region of from 1 mm to 3 mm, with the longitudinal extent of the exposed part of the return electrode being typically between 1 mm and 5 mm and the longitudinal spacing from the active electrode being between 1 mm and 5 mm. The electrode assembly 28 has an insulating sheath 42 which covers shaft 40 and terminates proximally of the ceramic insulator 34 to leave the distal end of shaft 40 exposed as the return electrode 36.

In operation as an instrument for cutting or removing tissue in a conductive fluid field, the electrode assembly 28 is applied as shown in FIG. 2 to the tissue 44 to be treated, the operation site being immersed in a normal saline (0.9% w/v) solution 46 immersing both the active electrode 30 and the return electrode 36.

The electrode assembly is effectively bipolar, with only one of the electrodes (active electrode 30) axially extending to the distal end of the unit. This means that the return electrode, in normal circumstances in a wet field, remains spaced from the tissue being treated and a current path exists between the tissue and the return electrode via the conductive liquid in contact with the return electrode. The conductive liquid 46 may be regarded, as far as the delivery of bipolar electrosurgical energy is concerned, as a low impedance extension of the tissue.

When sufficient r.f. voltage is applied between the electrodes 30, 36, power dissipation in the conductive liquid 46 causes the liquid to vaporise, initially forming small vapour bubbles on the surface of the active electrode 30, which ultimately coalesce until the electrode is completely enveloped in a pocket of vapour 50. Vapour pocket 50 is sustained by discharges 52 across the vapour pocket between the active electrode 30 and the vapour-to-saline interface. The majority of power dissipation now occurs within this pocket with consequent heating of the active electrode, the amount of energy dissipated being a function of the delivered power. By holding the active electrode 30 adjacent the surface of the tissue 44, as shown in FIG. 2, so that the vapour pocket intercepts the tissue surface, tissue removal occurs by cell rupture due to the arcing occurring between the electrode and the tissue.

This mode of operation can be maintained over a comparatively wide range of power levels, but increasing the delivered power beyond this range causes a rapid rise in electrode temperature, potentially damaging the electrode. The point at which this occurs depends on the speed with which heat can be removed from the electrode which, as will be appreciated, is affected by convection due to flow of the fluid 46 past the electrode 20, the proximity of the electrode 30 to the tissue and, in the worst case, burying of the electrode 30 in the tissue. It follows that, while a peak voltage limit may be established to prevent a runaway temperature rise at the electrode, such limit, to be effective, has to be set at a level which will prevent such a rise in the worst case thermal dissipation conditions.

In accordance with the present invention, delivery of r.f. power to the electrode is controlled by sensing the temperature of the electrode. This is done indirectly by monitoring the thermionic effect as will now be described with reference to FIGS. 3A and 3B.

Figure 3A:
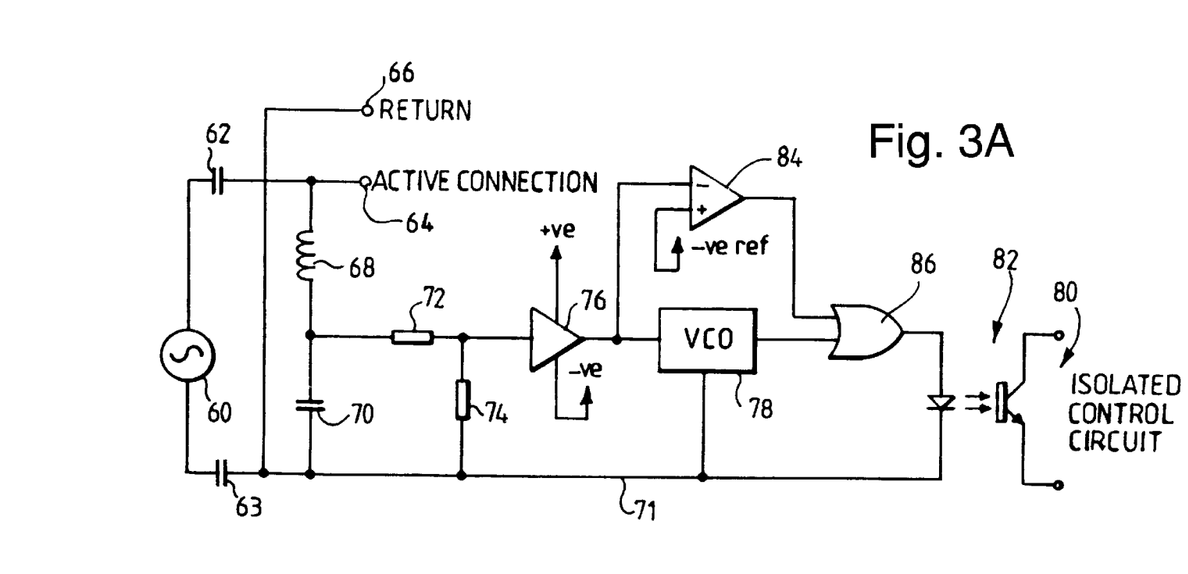
FIGS. 3A and 3B are circuit diagrams of an electrosurgery system including a d.c. offset detector.

Referring to FIG. 3A, a system in accordance with the invention includes an r.f. voltage source 60 delivering an electrosurgical voltage via coupling capacitors 62,63 between first and second output terminals 64, 66 to which the active and return electrodes of the electrosurgical instrument are respectively connected. When arcing occurs at the active electrode, as shown in FIG. 2, thermionic emission from the electrode occurs whilst the electrode is spaced from the tissue 44, dependent on the temperature of the electrode, leading to the build-up of a positive potential on the active output terminal 64. In effect, the combination of the heated active electrode 30, the tissue, the conductive fluid, and the return electrode together act as a rectifier, the conductive solution behaving as the anode and the active electrode as the cathode of the rectifier respectively. The hotter the active electrode, the greater is the rectification and the greater the d.c. offset voltage on the output terminal 64 of the generator.

The temperature-dependent positive potential (the d.c. offset voltage) is monitored using a detector having an input circuit with a series r.f. choke 68 coupled to the output terminal 64, and a smoothing capacitor 70 coupled to the common rail 71 which is connected to the return terminal 66. The d.c. component of the voltage at the active output terminal 64 therefore accumulates at the junction of the choke 68 and the smoothing capacitor 70 where it is applied to a potential divider 72, 74 which present an input resistance of at least 2 MΩ, and typically between 50 and 100 MΩ. The output of the potential divider 72, 74, is applied to a high impedance buffer 76 the output of which provides a driving signal to a voltage controlled oscillator (VCO) 78. Providing an input impedance in the region of 50 to 100 MΩ yields a detection current in the region of 1 μA for d.c. offsets in the region of 50 to 100 V. Maintaining a low detection current has the advantage that nerve stimulation due to a direct current between the target tissue and the return electrode is avoided.

Conversion of the d.c. offset voltage to an alternating signal in the VCO 78 allows a signal representative of the offset voltage level to be transmitted to an isolated control circuit (not shown) connected to the output 80 of the detector via an opto-isolator 82. An indication of the d.c. offset is thus communicated across the safety isolation barrier between the output terminals of the generator and the power generating and control circuitry. In the control circuitry, the alternating signal can be converted back to a d.c. level using a monostable and low pass filter, or may be counted by a gated counter and conveyed digitally. In either case, the control circuitry is arranged to reduce the voltage of source 60 when the d.c. offset voltage reaches a predetermined value (typically within the range 50 to 100 V). In this way, by selecting a threshold d.c. offset voltage related to the maximum safe operating temperature of the active electrode, the r.f. power delivered to the active electrode can be maximised in different thermal dissipation conditions.

When the bipolar electrode assembly shown in FIG. 2 is used incorrectly, for example when there is insufficient saline around the assembly, it is possible for arcing to occur at the return electrode 36. In such circumstances, the d.c. offset polarity reverses so that the active terminal 64 becomes negative with respect to the return. The detector illustrated in FIG. 3A includes a reverse polarity detection circuit in the form of a comparator 84 bypassing the VCO 78 and having an output coupled to one input of, for instance, an OR-gate 86 the other input of which receives the alternating output from the VCO 78. The other input of the comparator 84 is coupled to a negative voltage reference. Normally, the output of comparator 84 is low, which means that the alternating signal developed by the VCO passes through OR-gate 84 to the opto isolator 82. However, when the d.c. offset voltage on output terminal 64 of the generator turns negative by more than an amount depending on the negative reference voltage applied to comparator 84, the output of comparator 84 becomes high and OR-gate 86 blocks the alternating signal from the VCO 78, and the lack of an alternating signal applied to the control circuit from the detector output 80 can be used as a fault indication to shut off the r.f. voltage source 60.

Figure 3B:
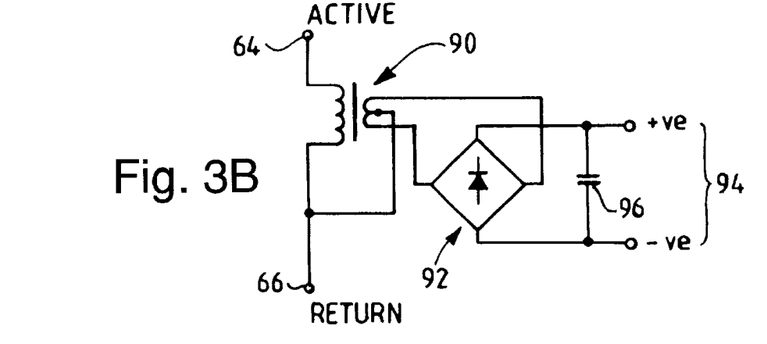

In this embodiment, power for the buffer 76, VCO 78, comparator 84, and OR-gate 86 is derived from the r.f. voltage itself delivered to the output terminals 64 and 66 of the generator, avoiding the need for a further isolation barrier. A suitable power supply for this purpose is illustrated in FIG. 3B. A step-down transformer 90 coupled between the output terminals 64 and 66 of the generator drives a bridge rectifier 92 to deliver a d.c. voltage at power supply output terminals 94 across a smoothing capacitor 96. Connection of the secondary winding of the transformer 90 with a centre tap to the return output terminal 66 and thus the common rail of the detector allows buffer 76 to be provided with a dual-polarity supply in order to accommodate positive and negative-going d.c. offset voltages. The fact that deriving power from the r.f. output in this way results in the detector being inoperative at low voltages is no disadvantage since the thermionic effect relied upon as the control stimulus does not occur until the r.f. output voltage of the generator reaches a level consistent with arcing at the active electrode.

Figure 4:
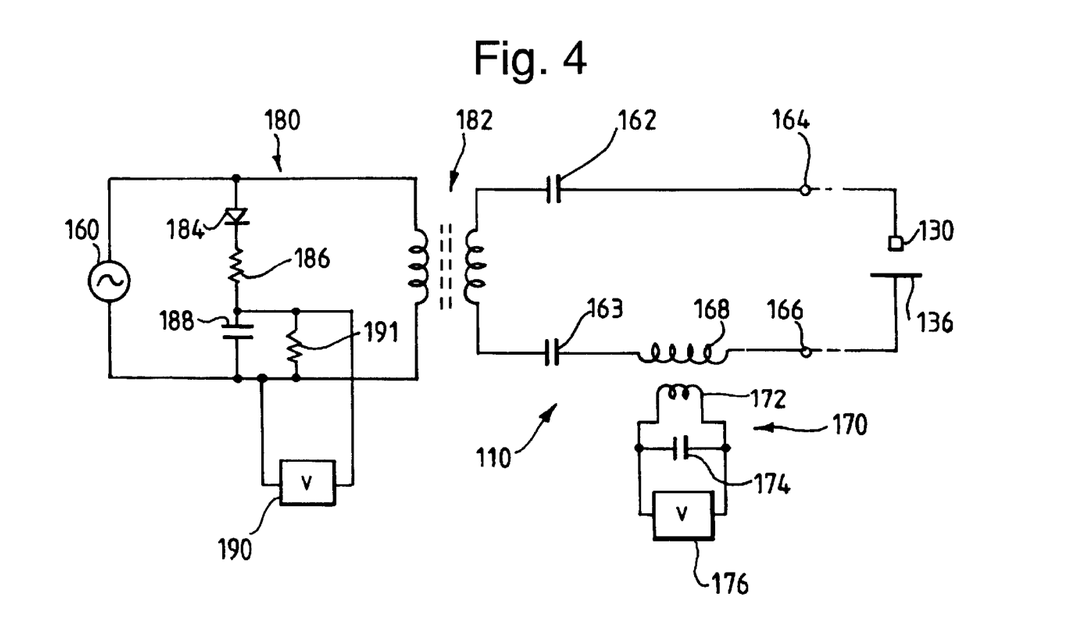
FIG. 4 is a circuit diagram of an alternative electrosurgery system in accordance with the invention.

Reference is now made to FIG. 4, which diagrammatically shows an alternative generator 110 in accordance with the invention, connected to an electrosurgical instrument having an active electrode 130 and a return electrode 136.

The output stage of the generator includes a pair of coupling capacitors 162, 163 which prevent the passage of DC currents between the radio frequency source and the electrodes 130, 136 via the generator output terminals 164, 166. In addition, the generator output stage includes an inductor 168 in series with the active and return electrodes 130, 136 respectively.

Figure 5:
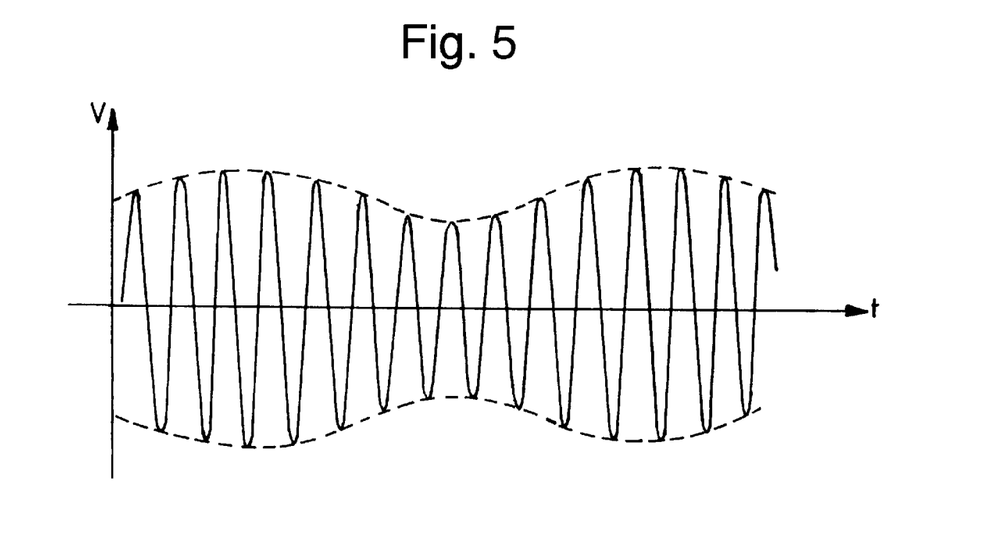
FIG. 5 is a waveform diagram showing the modulated output voltage waveform of the generator forming part of the system of FIG. 4.

Referring to FIG. 5, the output amplitude (i.e. the peak-to-peak output voltage at the output terminals 164, 166) of the generator is modulated, and in the present example a generator output signal is provided, having an output frequency of 500 kHz and amplitude modulated at a frequency of 25 kHz. Naturally, other generator and modulation frequencies may be employed. In the absence of any thermionic effect at the active electrode 136, the generator output voltage is symmetrical about the zero voltage line, i.e. because over a single time period of the generator output, an increase on the value of maximum positive output voltage with respect to the zero reference voltage is matched by a corresponding increase in maximum negative output voltage, the average value of the generator output signal as measured over a single modulation cycle of the generator output is constant.

Figure 6:
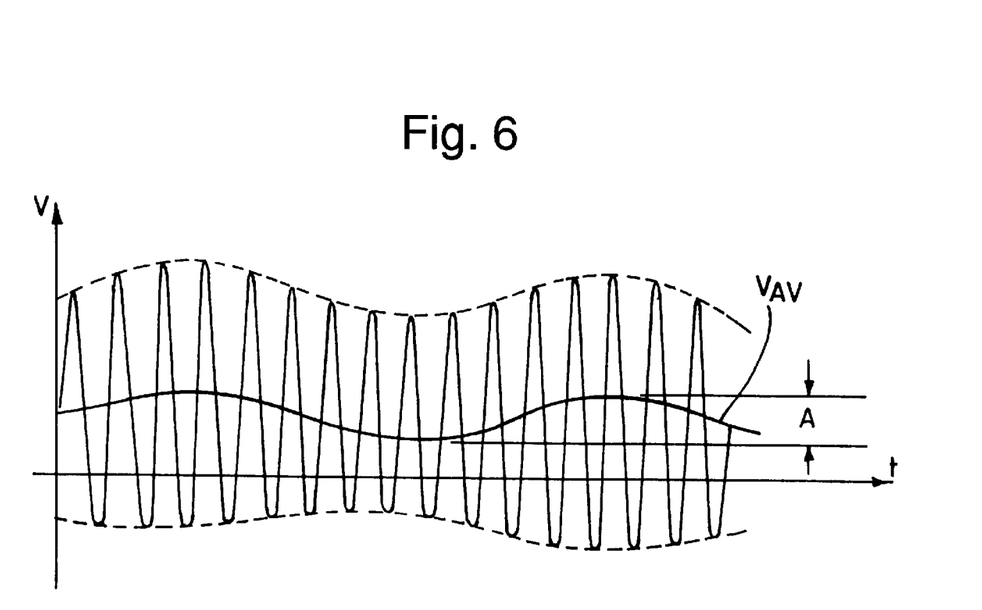
FIG. 6 is a waveform diagram showing the generator output waveform in the presence of a thermionic effect at the active electrode of the system illustrated in FIG. 4, as well as the average output voltage averaged over single radio frequency cycles of the output voltage.

However, once sufficient heating has occurred at the active electrode to cause thermionic emission of electrons from the active electrode, there is a net flow of electrons from the active electrode to the return electrode. There is, therefore, a net flow of current from the return electrode (which acts as the anode) to the active electrode (since the direction of current flow is defined as the flow of positive charge). Referring now to FIG. 6, this has the effect of shifting the modulated generator output voltage waveform in one direction, here the positive direction, so that rather than having an output voltage the average of which over a single cycle is constant at zero volts in a non-linear manner, the thermionic effect at the electrodes causes partial rectification of generator output and the average output voltage measured over a single cycle is now a non-zero voltage. The magnitude of this voltage varies at the frequency of the amplitude modulation (which in the present example is 25 kHz). This variation in average output voltage is denoted by the line $V_{AV}$ in FIG. 6. Moreover, the amplitude A of this variation in average output voltage is dependent upon the extent of the positive shift in the output of the generator, the maximum amplitude of the 25 kHz signal being twice the depth of the amplitude modulation. The amplitude A is a measure of the degree of net current flow from the return to the active electrode and, therefore, a measure of the thermionic effect at the active electrode which is, in turn, a measure of the active electrode temperature.

Referring once more to FIG. 4, in order to detect the 25 kHz variation in average output voltage which occurs as a result of the thermionic effect, the generator includes a sensing circuit 170 having a resonant circuit 172, 174 tuned to the modulation frequency, here 25 kHz, and including an alternating voltage sensing stage 176. The resonant circuit is parallel-resonant, its inductor 174 being inductively coupled to the output stage series inductor 168, the inductors forming an isolating transformer isolating the sensing circuit at DC from the output terminals 164, 166. When there is no thermionic effect at the active electrode 130, there is no net 25 kHz component to the generator output, since the fundamental generator output is a sinusoidal waveform at the generator operating frequency of 500 kHz, whose average value measured over a single cycle at the operating frequency remains constant at zero volts. Once thermionic emissions take place, the positive shift in the generator output introduces a 25 kHz component in the averaged generator output, the magnitude of this 25 kHz variation in the average value is detected in the AC voltage sensing stage 176, the output of which, as explained above, is directly indicative of the extent of thermionic effect at the active electrode 130 and, therefore, the temperature of the active electrode 130.

In a modification (not shown) the resonant circuit may be in the generator output circuit itself, for example, as a series-connected parallel resonant circuit comprising the inductor 168 and a capacitor connected in parallel with it. The voltage sensing stages may be inductively coupled to the resonant circuit via the inductor 168 in order to detect the modulation voltage across the resonant circuit.

The output of the voltage sensing stage 176 is coupled to a feedback circuit (not shown) which varies the absolute generator output amplitude (e.g. the maximum or minimum amplitude of the generator output, rather than the extent or depth of the amplitude modulation) in order to maintain a given pre-set temperature at the active electrode.

Ideally, the frequency of modulation is chosen such that the speed of changes in the thermionic emissions from the active electrode is slow in comparison with a single modulation period or cycle. At a modulation frequency of 25 kHz, the modulation period is 40 microseconds, which is significantly shorter than the response time of the DC coupled detection circuit of the embodiment described above with reference to FIGS. 3A and 3B.

The depth (i.e. amplitude or the extent) of the modulation in generator output voltage is ideally chosen according to the size of thermionic emissions to be detected. A relatively large depth of amplitude modulation in the generator output has the result that even a small shift or offset in the generator output will result in a significant variation in the average value of the generator output measured over a single cycle at the operating frequency, and thus will enable easy detection of relatively small thermionic emissions. In practice, the shift in average voltage brought about by the thermionic effect is in the region of 50 V, the peak-to-peak output voltage at the operating frequency being typically 100 V.

The illustrated generator output stage is effectively a resonant circuit whose resonant frequency varies with the impedance of the load at the electrodes 130, 136. If the resonant frequency of the generator output stage shifts relative to the operating frequency to an extent such that there is a drop in the generator output voltage which is much greater than the depth of the amplitude modulation, and which occurs over a time period which is short compared with the duration of a single modulation cycle of the generator output, the amplitude modulation is significantly changed by the relatively large variation in amplitude which occurs as a result of the changing resonance. Since, as mentioned above, the magnitude of the voltage detected by the a.c. voltmeter stage 176 for a given level of thermionic emission is a function of the depth of modulation of the generator output, what are effectively unrelated variations in the depth of such modulation caused by changes in the output stage resonance cause inaccuracies in the measurement of thermionic emission by the voltmeter 176. Put another way, although variations in the average value of the generator output measured over a single cycle would be representative of the existence of thermionic emissions, the magnitude of such variations would not necessarily represent the extent of such emissions, because of the possibility that there will be a variation in the depth of modulation as a result of varying resonance in the output stage of the generator.

Since the resonant frequency of the output circuit varies with load impedance, it is not possible simply to account for variations in resonance in advance, because it is not possible to know in advance when, or at what frequency they are likely to occur. Accordingly, the generator in the system of FIG. 4 includes a compensation arrangement, here including a modulation reference, for normalising the output from the voltmeter 176. Referring again to FIG. 4, this compensation arrangement has a detection circuit 180 connected across the primary winding of a generator output transformer 182. This modulation detection circuit 180 comprises a diode 184 in series with a resistor 196 and the capacitor 188. A voltmeter 190 and further resistor 191 are connected in parallel with the capacitor 188, and the voltmeter 190 detects the instantaneous depth of the modulation in the generator output, and this may be used to provide a modulation reference by means of which the output from the voltmeter 176 of the sensing circuit may effectively be normalised to reflect only the effect of the thermionic emissions at the electrode 130.

Use of the invention is not restricted to wet field (underwater) electrosurgery. Arcing also occurs with monopolar or bipolar electrosurgery instruments in dry field surgery and power can be controlled using the thermionic effect in the same way as described above. It is also possible to set the d.c. offset threshold voltage at a comparatively low level in order substantially to avoid nerve stimulation in situations where the active electrode intermittently contacts tissue.

In monopolar applications the intensity of arcing is dependent on the impedance of the conduction path between the arc site and the return electrode, low impedance increasing peak arc currents and hence temperature, cutting rate and nerve stimulation. It follows that controlling power according to electrode temperature (so as to reduce variation in electrode temperature) using thermionic effect sensing allows more consistent tissue action to be achieved. This can result in increased cutting quality, for instance, in that tissue damage and char formation adjacent the cutting site can be reduced compared with electrosurgical action relying on voltage control alone.

Thermionic feedback is an electrosurgical generator offers a number of benefits, including achieving increased tissue ablation and cutting rates, potentially reducing damage to adjacent tissue, and adjacent char formation, as well as reduced nerve stimulation.

Using the thermionic effect occurring in the presence of arcing at an electrode as the stimulus of a feedback mechanism, as described in this specification, allows electrosurgery to be performed at relatively high power intensities substantially without electrode damage. Thus, using a high melting point material such as platinum, very high tissue cutting and tissue removal power intensities may be achieved or, for a given power intensity, comparatively inexpensive, low melting point metals or alloys may be used with safety (e.g. stainless steel). The described system may also be used to reduce the possibility of electrode misuse and consequent electrode damage. The ability to maintain large arcs lessens the possibility of contact of the active electrode with tissue, therefore decreasing the possibility of nerve stimulation.

While the preferred embodiments of the invention are systems in which the thermionic effect is sensed by means of a circuit within an electrosurgical generator unit, i.e. within the casing of such a unit, it is possible to embody the invention in an add-on module coupled in the conduction paths between the output terminals of the generator unit and the electrosurgical instrument. The module may have its own connector which fits into the socket 10S of the generator unit and a socket for receiving a plug assembly on the connection cord 14 shown in FIG. 1. Circuitry for detecting an offset voltage is contained within the module, connected to lines forming the conduction paths between the generator unit and the instrument, and the transmission of electrosurgical power to the instrument controlled by means of a variable impedance element within the module or by feeding a control signal to a control input of the generator unit. For the avoidance of doubt, the combination of an add-on module of this description and a separate generator unit are considered to constitute an electrosurgical generator within the scope of the present invention as claimed.

Although the described embodiments perform a control function in that generator output power is controlled or regulated in response to the sensed thermionic effect, the invention includes within its scope a system in which the means for sensing thermionic emissions are used simply as an indicator of electrode temperature, e.g. for providing a temperature readout for the surgeon.

What is claimed is:

1. An electrosurgery system comprising a generator which includes a source of radio frequency (r.f.) energy for feeding to a treatment electrode of an electrosurgical instrument, the generator comprising:

a circuit for sensing thermionic emission from the treatment electrode, the sensing circuit having an input stage arranged substantially to remove r.f. signals at an operating frequency or frequencies of the generator to yield an averaged representation of r.f. output of the generator, and a detection stage coupled to the input stage to receive the averaged representation, wherein the generator is arranged to generate a modulated r.f. output for feeding to the treatment electrode of the electrosurgical instrument, and the sensing circuit is arranged such that substantial removal of the r.f. signals at the generator operating frequency results in an averaged signal being fed to the detection stage which produces a sensing circuit signal as a measure of an amplitude of the averaged signal;

wherein the sensing circuit input stage comprises a filter having a passband including the frequency of the modulation but excluding the generator operating frequency, the averaged signal being an a.c. signal having a frequency equal to the modulation frequency; and wherein the generator has an output stage having a pair of output lines coupled to respective generator output terminals, each output line having a series-connected isolation capacitor, and a series inductor in one of the output lines between the respective isolating capacitor and output terminal, the inductor being coupled to the input stage of the sensing circuit.

2. A system according to claim 1, wherein the input stage comprises a parallel resonant circuit tuned to the modulation frequency and having an inductance inductively coupled to said series inductance, and wherein the detection circuit is coupled across the resonant circuit to detect the amplitude of the signal developed across the resonant circuit.

3. An electrosurgical generator comprising a radio frequency (r.f.) power source operable at a generator operating frequency, and an output stage including a pair of r.f. power output terminals, the output stage being DC-isolated from the source, the generator further comprising means for modulating the r.f. power signal generated by the source, and a sensing circuit AC-coupled to and DC-isolated from the output stage and operable to generate an averaged AC signal containing a modulation component representative of a DC shift in the power signal delivered to the output terminals.

4. A generator according to claim 3, wherein the modulation means produces amplitude modulation in the r.f. power signal at a predetermined modulation frequency, and wherein the generator further comprises a filtering element associated with the sensing circuit for substantially removing an r.f. component at the operating frequency from the input to the sensing circuit to yield the averaged AC signal.

* * * * *